(12) United States Patent
Bergsma et al.

(10) Patent No.: US 6,423,508 B1
(45) Date of Patent: Jul. 23, 2002

(54) POLYNUCLEOTIDE SEQUENCES OF HUMAN EDG-1C

(75) Inventors: Derk J. Bergsma, Berwyn; Winnie Chan, West Chester, both of PA (US); Nassirah Khandoudi, Saint Gregoire (FR); Phillipe Robert, Saint Gregoire (FR)

(73) Assignees: SmithKline Beecham Corporation, Philadelphia, PA (US); SmithKline Beecham PLC, Brentford (GB); SB Laboratories Pharmaceutiques, Nanterre Cedex (FR)

( * ) Notice: Subject to any disclaimer, the term of this patent is extended or adjusted under 35 U.S.C. 154(b) by 0 days.

(21) Appl. No.: 09/262,477

(22) Filed: Mar. 4, 1999

Related U.S. Application Data

(60) Provisional application No. 60/077,369, filed on Mar. 9, 1998, and provisional application No. 60/087,102, filed on May 28, 1998.

(51) Int. Cl.⁷ .................................................. C12P 21/02
(52) U.S. Cl. ..................... 435/69.1; 530/350; 536/23.5; 435/320.1; 435/252.3; 435/325
(58) Field of Search ........................ 530/350; 536/23.5; 435/320.1, 252.3, 69.1

(56) References Cited

U.S. PATENT DOCUMENTS

| | | |
|---|---|---|
| 5,508,384 A | 4/1996 | Murphy et al. ............ 435/69.1 |
| 5,585,476 A | 12/1996 | MacLennan ................ 536/23.5 |
| 5,912,144 A | 6/1999 | Au-Young et al. ......... 435/69.1 |

FOREIGN PATENT DOCUMENTS

| | | |
|---|---|---|
| WO | WO91/15583 | 10/1991 |
| WO | WO98/48016 | 10/1998 |

OTHER PUBLICATIONS

Lee et al. "Sphingosine–1–Phosphate as a Ligand for the G Protein–Coupled Receptor EDG–1" *Science* 279: 1552–1555 (1998).

Zondag et al. "Sphingosine 1–phosphate signalling through the G–protein coupled receptor Edg–1" *Journal of Biochemistry* 330: 605–609 (1998).

Hla et al. "An Abundant Transcript Induced in Differentiating Human Endothelial Cells Encodes a Polypeptide with Structural Similarities to G–protein–coupled Receptor" The Journal of Biological Chemistry *The Journal of Biological Chemistry* 265(16): 9308–9313 (1990).

*Primary Examiner*—Lorraine Spector
*Assistant Examiner*—Eileen B. O'Hara
(74) *Attorney, Agent, or Firm*—Elizabeth J. Hecht; William T. King; Charles M. Kinig

(57) ABSTRACT

Human EDG-1c polypeptides and polynucleotides and methods for producing such polypeptides by recombinant techniques are disclosed. Human EDG-1c is identified as a selective receptor for sphingosine-1-phosphate ("S-1-P") and for di-hydro S-1-P. Also diclsosed are methods for discovering agonists and antagonists of the interaction between S-1-P and di-hydro S-1-P and their cellular receptor, human EDG-1c, which may have utility in the treatment of several human diseases and disorders.

8 Claims, 8 Drawing Sheets

Figure 1. Nucleotide sequence of human EDG-1c receptor (SEQ ID NO: 1).

```
ATGGGGCCCACCAGCGTCCCGCTGGTCAAGGCCCACCGCAGCTCGGTCTCTGACTACGTC
AACTATGATATCATCGTCCGGCATTACAACTACACGGGAAAGCTGAATATCAGCGCGGAC
AAGGAGAACAGCATTAAACTGACCTCGGTGGTGTTCATTCTCATCTGCTGCTTTATCATC
CTGGAGAACATCTTTGTCTTGCTGACCATTTGGAAAACCAAGAAATTCCACCGACCCATG
TACTATTTTATTGGCAATCTGGCCCTCTCAGACCTGTTGGCAGGAGTAGCCTACACAGCT
AACCTGCTCTTGTCTGGGGCCACCACCTACAAGCTCACTCCCGCCCAGTGGTTTCTGCGG
GAAGGGAGTATGTTTGTGGCCCTGTCAGCCTCCGTGTTCAGTCTCCTCGCCATCGCCATT
GAGCGCTATATCACAATGCTGAAAATGAAACTCCACAACGGGAGCAATAACTTCCGCCTC
TTCCTGCTAATCAGCGCCTGCTGGGTCATCTCCCTCATCCTGGGTGGCCTGCCTATCATG
GGCTGGAACTGCATCAGTGCGCTGTCCAGCTGCTCCACCGTGCTGCCGCTCTACCACAAG
CACTATATCCTCTTCTGCACCACGGTCTTCACTCTGCTTCTGCTCTCCATCGTCATTCTG
TACTGCAGAATCTACTCCTTGGTCAGGACTCGGAGCCGCCGCCTGACGTTCCGCAAGAAC
ATTTCCAAGGCCAGCCGCAGCTCTGAGAAGTCGCTGGCGCTGCTCAAGACCGTAATTATC
GTCCTGAGCGTCTTCATCGCCTGCTGGGCACCGCTCTTCATCCTGCTCCTGCTGGATGTG
GGCTGCAAGGTGAAGACCTGTGACATCCTCTTCAGAGCGGAGTACTTCCTGGTGTTAGCT
GTGCTCAACTCCGGCACCAACCCCATCATTTACACTCTGACCAACAAGGAGATGCGTCGG
GCCTTCATCCGGATCATGTCCTGCTGCAAGTGCCCGAGCGGAGACTCTGCTGGCAAATTC
AAGCGACCCATCATCGCCGGCATGGAATTCAGCCGCAGCAAATCGGACAATTCCTCCCAC
CCCCAGAAGACGAAGGGGACAACCCAGAGACCATTATGTCTTCTGGAAACGTCAACTCT
TCTTCCTAG
```

Figure 2. Deduced amino acid sequence of human EDG-1c receptor (SEQ ID NO: 2).

```
MGPTSVPLVKAHRSSVSDYVNYDIIVRHYNYTGKLNISADKENSIKLTSVVFILICCFII
LENIFVLLTIWKTKKFHRPMYYFIGNLALSDLLAGVAYTANLLLSGATTYKLTPAQWFLR
EGSMFVALSASVFSLLAIAIERYITMLKMKLHNGSNNFRLFLLISACWVISLILGGLPIM
GWNCISALSSCSTVLPLYHKHYILFCTTVFTLLLLSIVILYCRIYSLVRTRSRRLTFRKN
ISKASRSSEKSLALLKTVIIVLSVFIACWAPLFILLLLDVGCKVKTCDILFRAEYFLVLA
VLNSGTNPIIYTLTNKEMRRAFIRIMSCCKCPSGDSAGKFKRPIIAGMEFSRSKSDNSSH
PQKDEGDNPETIMSSGNVNSSS
```

Figure 4
Sphingosine-1-phosphate Signals through EDG1c
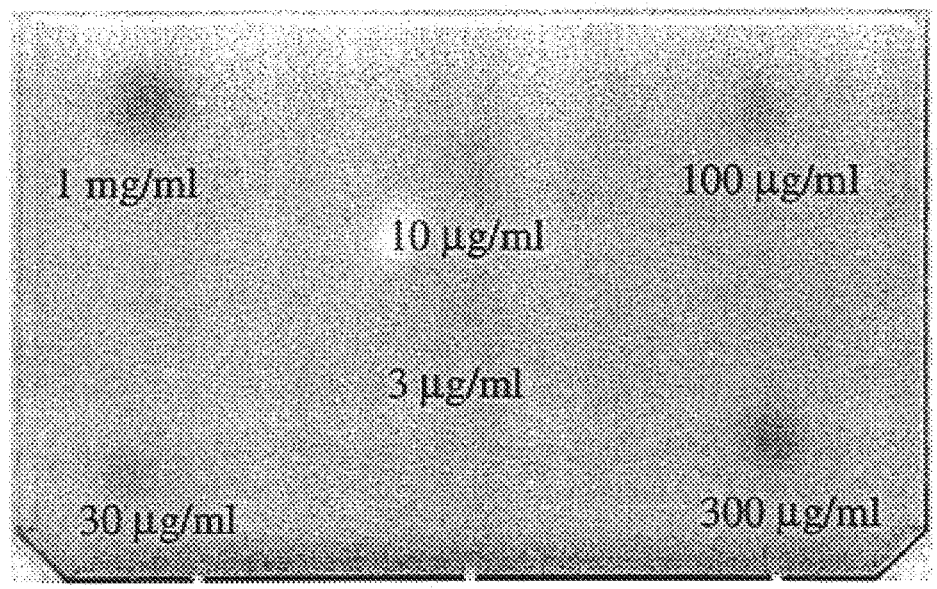
Gαi2
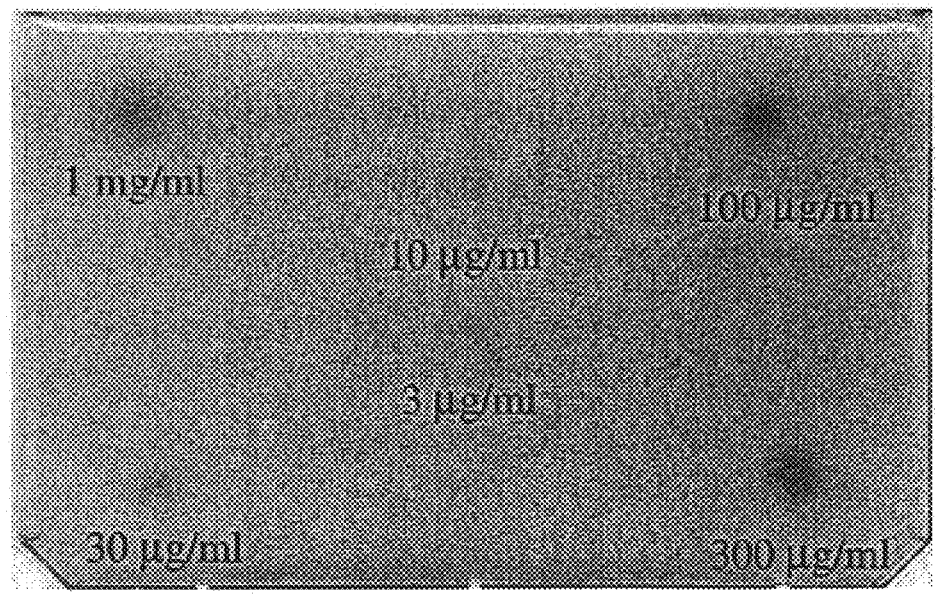
1 µl of each concentration spotted Activity of Shingosine-1-phosphate on the EDG1c Receptor Expressed in Yeast

POLYNUCLEOTIDE SEQUENCES OF HUMAN EDG-1C

CROSS-REFERENCE TO RELATED APPLICATION

This application claims benefit to the earlier provisional U.S. Application Nos. 60/077,369, filed on Mar. 9, 1998, and 60/087,102, filed on May 28, 1998, the contents of which are incorporated herein by reference in their entirety.

FIELD OF THE INVENTION

This invention relates to newly identified polypeptides and polynucleotides encoded by them and to the use of such polynucleotides and polypeptides, and to their production. More particularly, the polynucleotides and polypeptides of the present invention relate to the G-protein coupled receptors, hereinafter referred to as human EDG-1c receptor. This invention also relates to methods for discovering agonists and antagonists of the interaction between sphingosine 1-phosphate (hereinafter referred to as "S-1-P") and di-hydro sphingosine 1-phosphate (also kown as sphingoanine 1-phosphate and hereinafter referred to as "di-hydro S-1-P") and their cellular receptor, human EDG-1c receptor. The invention also relates to the use of human EDG-1c polynucleotides and polypeptides in therapy and in identifying compounds which may be agonists, antagonists and/or inhibitors which are potentially useful in therapy, and to production of such polypeptides and polynucleotides.

BACKGROUND OF THE INVENTION

The drug discovery process is currently undergoing a fundamental revolution as it embraces 'functional genomics', that is, high throughput genome- or gene-based biology. This approach is rapidly superseding earlier approaches based on 'positional cloning'. A phenotype, that is a biological function or genetic disease, would be identified and this would then be tracked back to the responsible gene, based on its genetic map position.

Functional genomics relies heavily on the various tools of bioinformatics to identify gene sequences of potential interest from the many molecular biology databases now available. There is a continuing need to identify and characterize further genes and their related polypeptides/proteins, as targets for drug discovery.

It is well established that many medically significant biological processes are mediated by proteins participating in signal transduction pathways that involve G-proteins and/or second messengers, e.g., cAMP (Lefkowitz, *Nature*, 1991, 351:353–354). Herein, these proteins are referred to as proteins participating in pathways with G-proteins. Some examples of these proteins include the G-protein coupled receptors, such as those for adrenergic agents and dopamine (Kobilka, B. K., et al., *Proc. Natl Acad. Sci., USA*, 1987, 84:46–50; Kobilka, B. K., et al., *Science*, 1987, 238:650–656; Bunzow, J. R., et al., *Nature*, 1988, 336:783–787), G-proteins themselves, effector proteins, e.g., phospholipase C, adenyl cyclase, and phosphodiesterase, and actuator proteins, e.g., protein kinase A and protein kinase C (Simon, M. I., et al., *Science*, 1991, 252:802–8).

For example, in one form of signal transduction, the effect of hormone binding is activation of the enzyme, adenylate cyclase, inside the cell. Enzyme activation by hormones is dependent on the presence of the nucleotide GTP. GTP also influences hormone binding. A G-protein connects the hormone receptor to adenylate cyclase. G-protein was shown to exchange GTP for bound GDP when activated by a hormone receptor. The GTP-carrying form then binds to activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane a-helices connected by extracellular or cytoplasmic loops. G-protein coupled receptors include a wide range of biologically active receptors, such as hormone, viral, growth factor and neuroreceptors.

G-protein coupled receptors (otherwise known as 7TM receptors) have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include, but are not limited to, calcitonin, adrenergic, endothelin, cAMP, adenosine, muscarinic, acetylcholine, serotonin, histamine, thrombin, kinin, follicle stimulating hormone, opsins, endothelial differentiation gene-1, rhodopsins, odorant, and cytomegalovirus receptors.

Most G-protein coupled receptors have single conserved cysteine residues in each of the first two extracellular loops which form disulfide bonds that are believed to stabilize functional protein structure. The 7 transmembrane regions are designated as TM1, TM2, TM3, TM4, TM5, TM6, and TM7. TM3 has been implicated in signal transduction.

Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the b-adrenoreceptor, phosphorylation by protein kinase A and/or specific receptor kinases mediates receptor desensitization.

For some receptors, the ligand binding sites of G-protein coupled receptors are believed to comprise hydrophilic sockets formed by several G-protein coupled receptor transmembrane domains, said socket being surrounded by hydrophobic residues of the G-protein coupled receptors. The hydrophilic side of each G-protein coupled receptor transmembrane helix is postulated to face inward and form polar ligand binding site. TM3 has been implicated in several G-protein coupled receptors as having a ligand binding site, such as the TM3 aspartate residue. TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters (see, Johnson, et al., *Endoc. Rev.*, 1989, 10:317–331) Different G-protein a-subunits preferentially stimulate particular effectors to modulate various biological functions in a cell. Phosphorylation of cytoplasmic residues of G-protein coupled receptors have been identified as an important mechanism for the regulation of G-protein coupling of some G-protein coupled receptors. G-protein coupled receptors are found in numerous sites within a mammalian host.

Over the past 15 years, nearly 350 therapeutic agents targeting 7 transmembrane (7 TM) receptors have been successfully introduced onto the market.

SUMMARY OF THE INVENTION

In one aspect, the invention relates human EDG-1c polypeptides and recombinant materials and methods for their production. Another aspect of the invention relates to methods for using such human EDG-1c polypeptides and polynucleotides. Such uses include the treatment of infections such as bacterial, fungal, protozoan and viral infections, particularly infections such as bacterial, fungal, protozoan and viral infections, particularly infections caused by HIV-1 or HIV-2; pain; cancers; diabetes, obesity; anorexia; bulimia; asthma; Parkinson's disease; acute heart failure; hypotension; hypertension; urinary retention; osteoporosis; angina pectoris; myocardial infarction; stroke; congestive heart failure; left ventricular hypertrophy; arrythmias; restenosis after coronary artery angioplasty; vascular sclerosis; deleterious fibrosis; atherosclerosis; inflammation; angiogenesis; wound healing; ulcers; asthma; allergies; benign prostatic hypertrophy; migraine; vomiting; psychotic and neurological disorders, including anxiety, schizophrenia, manic depression, depression, delirium, dementia, and severe mental retardation; degenerative diseases, such as neurodegenerative diseases and ischemic stroke; and dyskinesias, such as Huntington's disease or Gilles dela Tourett's syndrome, among others In accordance with another aspect of the present invention there are provided methods of screening for compounds which bind to and activate (agonist) or inhibit activation (antagonist) of human EDG-1c polypeptides (receptors), and for their ligands.

In particular, the preferred method for identifying agonist or antagonist of a human EDG-1c polypeptide comprises:

(a) contacting a cell expressing on the surface thereof the polypeptide, said polypeptide being associated with a second component capable of providing a detectable signal in response to the binding of a compound to said polypeptide, with a compound to be screened under conditions to permit binding to the polypeptide; and (b) determining whether the compound binds to and activates or inhibits the polypeptide by measuring the level of a signal generated from the interaction of the compound with the polypeptide.

In a further preferred embodiment, the method further comprises conducting the identification of agonist or antagonist in the presence of labeled or unlabeled S-1-P or di-hydro S-1-P.

In another embodiment, the method for identifying agonist or antagonist of a human EDG-1c polypeptide comprises:

determining the inhibition of binding of a ligand to cells which have the polypeptide on the surface thereof, or to cell membranes containing the polypeptide, in the presence of a candidate compound under conditions to permit binding to the polypeptide, and determining the amount of ligand bound to the polypeptide, such that a compound capable of causing reduction of binding of a ligand is an agonist or antagonist. Preferably, the ligand is S-1-P or di-hydro S-1-P. Yet more preferably, S-1-P or di-hydro S-1-P is labeled.

Furthermore, the present invention relates to treating conditions associated with human EDG-1c receptor imbalance with the identified compounds. Yet another aspect of the invention relates to diagnostic assays for detecting diseases associated with inappropriate EDG-1 activity or levels.

BRIEF DESCRIPTION OF THE DRAWINGS

FIG. 1 shows the nucleotide sequence of the human EDG-1c receptor (SEQ ID NO:1).

FIG. 2 shows the deduced amino acid sequence of the human EDG-1c receptor (SEQ ID NO:2).

FIG. 4 shows an agar plate assay of the dose response for S-1-P against yeast cells containing the pathway-inducible fus1-lacZ reporter and expressing the human EDG-1c receptor in combination with either the endogenous yeast G? protein (GPA1) or a chimeric yeast G?/human G?i2.

DESCRIPTION OF THE INVENTION

Definitions

Figure 3:
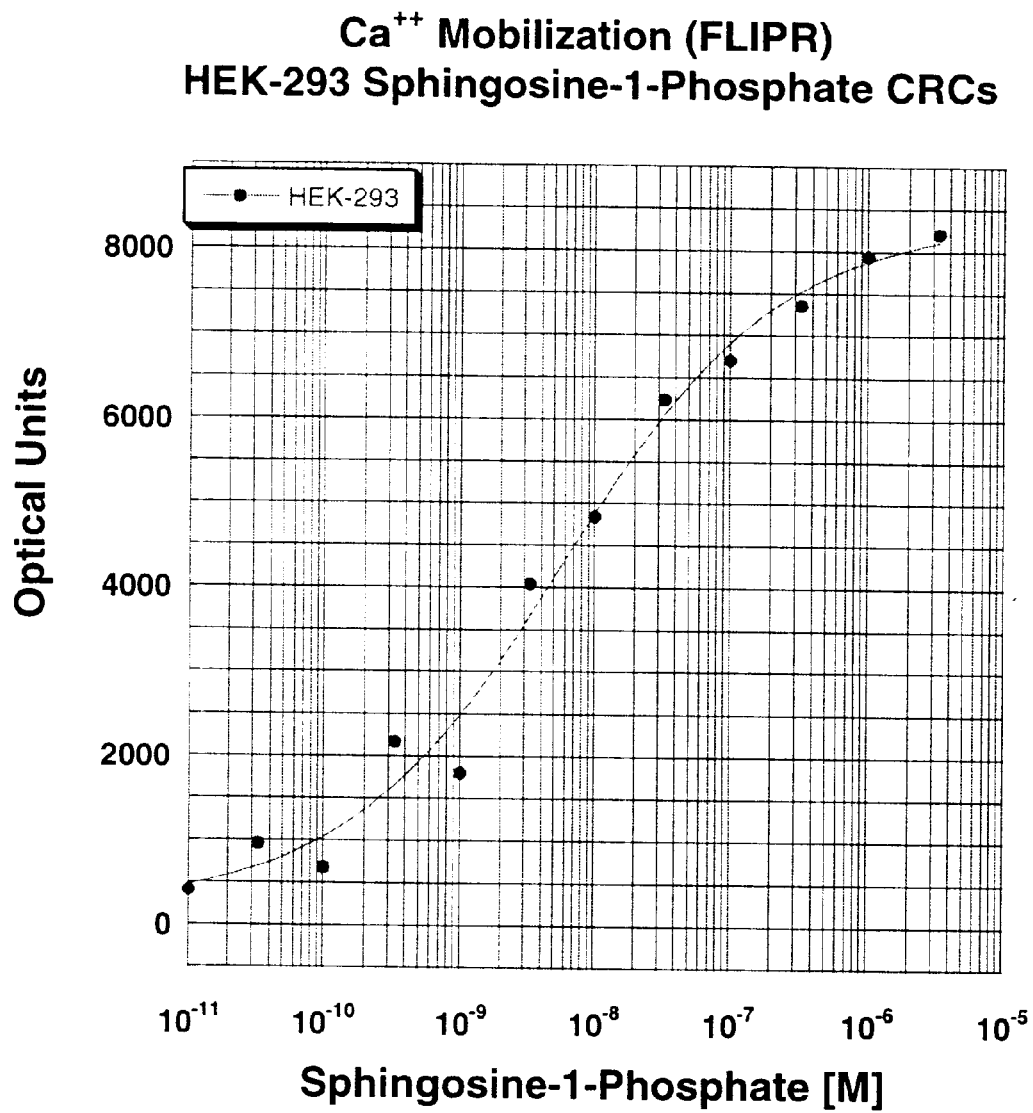
FIG. 3 shows concentration response curves for S-1-P against endogeneous HEK293 cells.

The following definitions are provided to facilitate understanding of certain terms used frequently herein.

"Human EDG-1c" refers generally to polypeptides having the amino acid sequence set forth in SEQ ID NO:2 or an allelic variant thereof.

"S-1-P (sphingosine-1-phosphate)" refers to the sphingolipid metabolite having the structure:

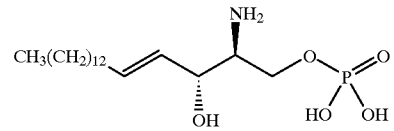

"Di-hydro S-1-P" (di-hydro sphingosine-1-phosphate)" (hereinafter referred to as "di-hydro S-1-P") refers to the sphingolipid metabolite having the structure:

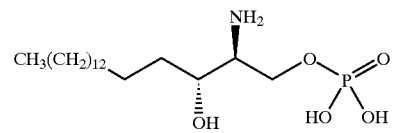

"Receptor Activity" or "Biological Activity of the Receptor" refers to the metabolic or physiologic function of said human EDG-1c including similar activities or improved activities or these activities with decreased undesirable side-effects. Also included are antigenic and immunogenic activities of said human EDG-1c.

"Human EDG-1c polypeptides" refers to polypeptides with amino acid sequences sufficiently similar to human EDG-1c preferably exhibiting at least one biological activity of the receptor.

"Human EDG-1c gene" refers to a polynucleotide having the nucleotide sequence set forth in SEQ ID NO:1 or allelic variants thereof and/or their complements.

"Human EDG-1c polynucleotides" and refers to polynucleotides containing a nucleotide sequence which encodes a human EDG-1c polypeptide of SEQ ID NO:2, or a nucleotide sequence which has sufficient identity to a nucleotide sequence contained in SEQ ID NO:1 to hybridize under conditions useable for amplification or for use as a probe or marker.

"Antibodies," as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enymol* (1990) 182:626–646 and Rattan, et al., "Protein Synthesis: Posttranslational Modifications and Aging", *Ann NY Acad Sci* (1992) 663:48–62.

"Variant," as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data,* Part I, Griffin, A. M., and Griffin, H. G., eds., Humana Press, New Jersey, 1994; *Sequence Analysis in Molecular Biology,* von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1): 387 (1984)), BLASTP, BLASTN, and FASTA (Altschul, et al., *J. Molec. Biol.* 215: 403–410 (1990). The BLAST X program is publicly available from NCBI and other sources (*BLAST Manual*, Altschul, et al., NCBI NLM NIH Bethesda, Md. 20894; Altschul, S., et al., *J. Mol. Biol.* 215: 403–410 (1990). The well known Smith Waterman algorithm may also be used to determine identity.

Preferred parameters for polypeptide sequence comparison include the following:
1) Algorithm: Needleman and Wunsch, *J. Mol Biol.* 48: 443–453 (1970)
Comparison matrix: BLOSSUM62 from Hentikoff and Hentikoff, *Proc. Natl. Acad. Sci. USA.* 89:10915–10919 (1992)
Gap Penalty: 12
Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Preferred parameters for polynucleotide comparison include the following:
1) Algorithm: Needleman and Wunsch, *J. Mol Biol.* 48: 443–453 (1970)
Comparison matrix: matches=+10, mismatch=0
Gap Penalty: 50
Gap Length Penalty: 3
Available as: The "gap" program from Genetics Computer Group, Madison Wis. These are the default parameters for nucleic acid comparisons.

By way of example, a polynucleotide sequence of the present invention may be identical to the reference sequence of SEQ ID NO:1, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in SEQ ID NO:1 by the numerical percent of the respective percent identity (divided by 100) and subtracting that product from said total number of nucleotides in SEQ ID NO:1, or:

$$n_n 23\ x_n - (x_n \cdot y),$$

wherein $n_n$ is the number of nucleotide alterations, $x_n$ is the total number of nucleotides in SEQ ID NO:1, and y is, for instance, 0.70 for 70%, 0.80 for 80%, 0.85 for 85%, 0.90 for 90%, 0.95 for 95%, etc., and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

Similarly, a polypeptide sequence of the present invention may be identical to the reference sequence of SEQ ID NO:2, that is be 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the numerical percent of the respective percent identity (divided by 100) and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, and y is, for instance 0.70 for 70%, 0.80 for 80%, 0.85 for 85% etc., and wherein any non-integer product of $x_a$ and y is rounded down to the nearest integer prior to subtracting it from $x_a$.

Polypeptides of the Invention

The human EDG-1c polypeptides of the present invention include the polypeptide of SEQ ID NO:2 (in particular the mature polypeptide).

The human EDG-1c polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Biologically active fragments of the human EDG-1c polypeptides are also included in the invention. A fragment is a polypeptide having an amino acid sequence that entirely is the same as part, but not all, of the amino acid sequence of the aforementioned human EDG-1c polypeptides. As with human EDG-1c polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of human EDG-1c polypeptides. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of human EDG-1c polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Biologically active fragments are those that mediate receptor activity, including those with a similar activity or an improved activity, or with a decreased undesirable activity. Also included are those that are antigenic or immunogenic in an animal, especially in a human.

Thus, the polypeptides of the invention include polypeptides having the amino acid sequence set forth in SEQ ID NO:2. Preferably, all of these polypeptides retain the biological activity of the receptor, including antigenic activity. Included in this group are variants of the defined sequence and fragments. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The human EDG-1c polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to isolated polynucleotides which encode the EDG-1 polypeptides and polynucleotides closely related thereto.

The nucleotide sequence of SEQ ID NO:1 shows homology with human EDG-1 receptor (Hla, T., and T. Maciag; 1990; *J. Biol. Chem.* 265: 9309–9313). The nucleotide sequence of SEQ ID NO:1 is a cDNA sequence and comprises a polypeptide encoding sequence (nucleotide 1 to 1149) encoding a polypeptide of 382 amino acids, the polypeptide of SEQ ID NO:2. The nucleotide sequence encoding the polypeptide of SEQ ID NO:2 may be identical to the polypeptide encoding sequence contained in SEQ ID NO:1 or it may be a sequence other than the one contained in SEQ ID NO:1, which, as a result of the redundancy (degeneracy) of the genetic code, also encodes the polypeptide of SEQ ID NO:2. The polypeptide of the SEQ ID NO:2 is structurally related to other proteins of the G-coupled Protein Receptors family, having homology and/or structural similarity with human EDG-1 receptor (Hla, T., and T. Maciag; 1990; *J. Biol. Chem.* 265: 9309–9313).

One polynucleotide of the present invention encoding human EDG-1c may be obtained using standard cloning and screening, from a cDNA library derived from mRNA in cells of human placenta using the expressed sequence tag (EST) analysis (Adams, M. D., et al. *Science* (1991) 252:1651–1656; Adams, M. D. et al., *Nature*, (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

Thus, the nucleotide sequence encoding human EDG-1c polypeptides may be identical over its entire length to the coding sequence in FIG. 1 (SEQ ID NO:1).

When the polynucleotides of the invention are used for the recombinant production of human EDG-1c polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or prepro- protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz, et al., *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Among particularly preferred embodiments of the invention are polynucleotides encoding human EDG-1c polypeptides having the amino acid sequence of set out in FIG. 1 (SEQ ID NO:2) and variants thereof.

Further preferred embodiments are polynucleotides encoding human EDG-1c variants that have the amino acid sequence of the human EDG-1c of FIG. 1 (SEQ ID NO:2) in which several, 5–10, 1–5, 1–3, 1–2 or 1 amino acid residues are substituted, deleted or added, in any combination.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

Polynucleotides of the invention, which are sufficiently identical to a nucleotide sequence contained in SEQ ID NO:1, may be used as hybridization probes for cDNA and genomic DNA, to isolate full-length cDNAs and genomic clones encoding human EDG-1c and to isolate cDNA and genomic clones of other genes that have a high sequence similarity to the human EDG-1c gene. Such hybridization techniques are known to those of skill in the art. Typically these nucleotide sequences are 70% identical, preferably 80% identical, more preferably 90% identical to that of the reference sequence. The probes generally will comprise at least 15 nucleotides. Preferably, such probes will have at least 30 nucleotides and may have at least 50 nucleotides. Particularly preferred probes will range between 30 and 50 nucleotides.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis, et al., BASIC METHODS IN MOLECULAR BIOLOGY (1986) and Sambrook, et al., MOLECULAR CLONING: A LABORATORY MANUAL, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, E. coli, Streptomyces and Bacillus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook, et al., MOLECULAR CLONING, A LABORATORY MANUAL (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the human EDG-1c polypeptide is to be expressed for use in screening assays, generally, it is preferred that the polypeptide be produced at the surface of the cell. In this event, the cells may be harvested prior to use in the screening assay. If human EDG-1c polypeptide is secreted into the medium, the medium can be recovered in order to recover and purify the polypeptide; if produced intracellularly, the cells must first be lysed before the polypeptide is recovered.

Human EDG-1c polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of human EDG-1c polynucleotides for use as diagnostic reagents. Detection of a mutated form of human EDG-1c gene associated with a dysfunction will provide a diagnostic tool that can add to or define a diagnosis of a disease or susceptibility to a disease which results from under-expression, over-expression or altered expression of human EDG-1c. Individuals carrying mutations in the human EDG-1c gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled human EDG-1c nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers, et al., Science (1985) 230:1242. Sequence changes at specific locations may also be revealed by nuclease protection assays, such as RNase and S1 protection or the chemical cleavage method. See Cotton, et al., Proc Natl Acad Sci USA (1985) 85:4397–4401.

The diagnostic assays offer a process for diagnosing or determining a susceptibility to infections such as bacterial, fungal, protozoan and viral infections, particularly through detection of mutation in the EDG-1 gene by the methods described.

In addition, infections such as bacterial, fungal, protozoan and viral infections, particularly infections such as bacterial, fungal, protozoan and viral infections, particularly infections caused by HIV-1 or HIV-2; pain; cancers; diabetes, obesity; anorexia; bulimia; asthma; Parkinson's disease; acute heart failure; hypotension; hypertension; urinary retention; osteoporosis; angina pectoris; myocardial infarction; stroke; congestive heart failure; left ventricular hypertrophy; arrythmias; restenosis after coronary artery angioplasty; vascular sclerosis; deleterious fibrosis; atherosclerosis; inflammation; angiogenesis; wound healing; ulcers; asthma; allergies; benign prostatic hypertrophy; migraine; vomiting; psychotic and neurological disorders, including anxiety, schizophrenia, manic depression, depression, delirium, dementia, and severe mental retardation; degenerative diseases, such as neurodegenerative diseases and ischemic stroke; and dyskinesias, such as Huntington's disease or Gilles dela Tourett's syndrome, can be diagnosed by methods comprising determining from a sample derived from a subject an abnormally decreased or increased level of human EDG-1c polypeptide or human EDG-1c mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as human EDG-1c, in a sample derived from a host are well-known to those of skill in the art. Such assay methods include radioimmunoassays, competitive-binding assays, Western Blot analysis and ELISA assays.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them can also be used as immunogens to produce antibodies immunospecific for the human EDG-1c polypeptides. The term "immunospecific" means that the antibodies have substantially greater affinity for the polypeptides of the invention than their affinity for other related polypeptides in the prior art.

Antibodies generated against the human EDG-1c polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor, et al., *Immunology Today* (1983) 4:72) and the EBV-hybridoma technique (Cole, et al., *MONOCLONAL ANTIBODIES AND CANCER THERAPY*, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against human EDG-1c polypeptides may also be employed to treat infections such as bacterial, fungal, protozoan and viral infections, particularly infections such as bacterial, fungal, protozoan and viral infections, particularly infections caused by HIV-1 or HIV-2; pain; cancers; diabetes, obesity; anorexia; bulimia; asthma; Parkinson's disease; acute heart failure; hypotension; hypertension; urinary retention; osteoporosis; angina pectoris; myocardial infarction; stroke; congestive heart failure; left ventricular hypertrophy; arrythmias; restenosis after coronary artery angioplasty; vascular sclerosis; deleterious fibrosis; atherosclerosis; inflammation; angiogenesis; wound healing; ulcers; asthma; allergies; benign prostatic hypertrophy; migraine; vomiting; psychotic and neurological disorders, including anxiety, schizophrenia, manic depression, depression, delirium, dementia, and severe mental retardation; degenerative diseases, such as neurodegenerative diseases and ischemic stroke; and dyskinesias, such as Huntington's disease or Gilles dela Tourett's syndrome, among others.

Vaccine

Another aspect of the invention relates to a method for inducing an immunological response in a mammal which comprises inoculating the mammal with human EDG-1c polypeptide, or a fragment thereof, adequate to produce antibody and/or T cell immune response to protect said animal from infections such as bacterial, fungal, protozoan and viral infections, particularly infections such as bacterial, fungal, protozoan and viral infections, particularly infections caused by HIV-1 or HIV-2; pain; cancers; diabetes, obesity; anorexia; bulimia; asthma; Parkinson's disease; acute heart failure; hypotension; hypertension; urinary retention; osteoporosis; angina pectoris; myocardial infarction; stroke; congestive heart failure; left ventricular hypertrophy; arrythmias; restenosis after coronary artery angioplasty; vascular sclerosis; deleterious fibrosis; atherosclerosis; inflammation; angiogenesis; wound healing; ulcers; asthma; allergies; benign prostatic hypertrophy; migraine; vomiting; psychotic and neurological disorders, including anxiety, schizophrenia, manic depression, depression, delirium, dementia, and severe mental retardation; degenerative diseases, such as neurodegenerative diseases and ischemic stroke; and dyskinesias, such as Huntington's disease or Gilles dela Tourett's syndrome, among others. Yet another aspect of the invention relates to a method of inducing immunological response in a mammal which comprises, delivering human EDG-1c gene via a vector directing expression of human EDG-1c polypeptide in vivo in order to induce such an immunological response to produce antibody to protect said animal from diseases.

A further aspect of the invention relates to an immunological/vaccine formulation (composition) which, when introduced into a mammalian host, induces an immunological response in that mammal to a human EDG-1c polypeptide wherein the composition comprises a human EDG-1c polypeptide or human EDG-1c gene. The vaccine formulation may further comprise a suitable carrier. Since human EDG-1c polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The EDG1-c polypeptide of the present invention may be employed in a process for screening for compounds that bind to and activate the EDG1-c polypeptides of the present invention (called agonists), or inhibit the interaction of the EDG1-c polypeptides with receptor ligands (called antagonists). Thus, polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See Coligan, et al., Current Protocols in Immunology 1(2):Chapter 5 (1991).

EDG1-c proteins are responsible for many biological functions, including many pathologies. Provided by the invention are screening methods to identify compounds and drugs that stimulate EDG1-c or that inhibit the function or level of the polypeptide. In general, agonists are employed for therapeutic and prophylactic purposes for such conditions as infections such as bacterial, fungal, protozoan and viral infections, particularly infections caused by HIV-1 or HIV-2; pain; cancers; diabetes, obesity; anorexia; bulimia; asthma; Parkinson's disease; acute heart failure; hypotension; hypertension; urinary retention; osteoporosis; angina pectoris; myocardial infarction; stroke; congestive heart failure; left ventricular hypertrophy; arrythmias; restenosis after coronary artery angioplasty; vascular sclerosis; deleterious fibrosis; atherosclerosis; inflammation; angiogenesis; wound healing; ulcers; asthma; allergies; benign prostatic hypertrophy; migraine; vomiting; psychotic and neurological disorders, including anxiety, schizophrenia, manic depression, depression, delirium, dementia, and severe mental retardation; degenerative diseases, such as neurodegenerative diseases and ischemic stroke; and dyskinesias, such as Huntington's disease or Gilles dela Tourett's syndrome, among others.

In general, such screening procedures involve providing appropriate cells that express the receptor polypeptide of the present invention on the surface thereof. Such cells include cells from mammals, yeast, Drosophila or *E. coli*. In particular, a polynucleotide encoding the receptor of the present invention is employed to transfect cells to thereby express the EDG1-c polypeptide. The expressed receptor is then contacted with a test compound to observe binding, stimulation or inhibition of a functional response.

One such screening procedure involves the use of melanophores that are transfected to express the EDG1-c polypeptide of the present invention. Such a screening technique is described in PCT WO 92/01810, published Feb. 6, 1992. Such an assay may be employed to screen for a compound which inhibits activation of the receptor polypeptide of the present invention by contacting the melanophore cells that encode the receptor with both a receptor ligand, such as S-1-P or di-hydro S-1-P, and a compound to be screened. Inhibition of the signal generated by the ligand indicates that a compound is a potential antagonist for the receptor, i.e., inhibits activation of the receptor.

The technique may also be employed for screening of compounds that activate the receptor by contacting such cells with compounds to be screened and determining whether such compound generates a signal, i.e., activates the receptor.

Other screening techniques include the use of cells which express the EDG1-c polypeptide (for example, transfected CHO cells) in a system that measures extracellular pH changes caused by receptor activation. In this technique, compounds may be contacted with cells expressing the receptor polypeptide of the present invention. A second messenger response, e.g., signal transduction or pH changes, is then measured to determine whether the potential compound activates or inhibits the receptor.

Another screening technique involves expressing the EDG1-c polypeptide in which the receptor is linked to phospholipase C or D. Representative examples of such cells include, but are not limited to: endothelial cells, smooth muscle cells, and embryonic kidney cells. The screening may be accomplished as hereinabove described by detecting activation of the receptor or inhibition of activation of the receptor from the phospholipase second signal.

Another method involves screening for compounds that are antagonists, and thus inhibit activation of the receptor polypeptide of the present invention by determining inhibition of binding of labeled ligand, such as S-1-P or di-hydro S-1-P, to cells expressing the receptor on their surface, or cell membranes containing the receptor. Such a method involves transfecting a eukaryotic cell with DNA encoding the EDG1-c polypeptide, such that the cell expresses the receptor on its surface. The cell is then contacted with a potential antagonist in the presence of a labeled form of a ligand, such as S-1-P or di-hydro S-1-P. The ligand can be labeled, e.g., by radioactivity. The amount of labeled ligand bound to the receptors is measured, e.g., by measuring radioactivity associated with transfected cells or membrane from these cells. If the compound binds to the receptor, the binding of labeled ligand to the receptor is inhibited as determined by a reduction of labeled ligand which binds to the receptors. This method is called binding assay. Naturally, this same technique can be used to look for an agonist.

The screening method may simply measure the binding of a candidate compound to the polypeptide, or to cells or membranes bearing the polypeptide, or a fusion protein thereof by means of a label directly or indirectly associated with the candidate compound. Alternatively, the screening method may involve measuring or, qualitatively or quantitatively, detecting the competition of binding of a candidate compound to the polypeptide with a labeled competitor (e.g. agonist or antagonist). Further, these screening methods may test whether the candidate compound results in a signal generated by activation or inhibition of the polypeptide, using detection systems appropriate to the cells bearing the polypeptide. Inhibitors of activation are generally assayed in the presence of a known agonist and the effect on activation by the agonist by the presence of the candidate compound is observed. Further, the screening methods may simply comprise the steps of mixing a candidate compound with a solution containing a polypeptide of the present invention, to form a mixture, measuring EDG-1c activity in the mixture, and comparing the EDG-1c activity of the mixture to a control mixture which contains no candidate compound.

Another screening procedure involves the use of mammalian cells (CHO, HEK 293, Xenopus Oocytes, RBL-2H3, etc.) that are transfected to express the receptor of interest. The cells are loaded with an indicator dye that produces a fluorescent signal when bound to calcium, and the cells are contacted with a test substance and a receptor agonist, such as S-1-P or di-hydro S-1-P. Any change in fluorescent signal is measured over a defined period of time using, for example, a fluorescence spectrophotometer or a fluorescence imaging plate reader. A change in the fluorescence signal pattern generated by the ligand indicates that a compound is a potential antagonist or agonist for the receptor.

Another screening procedure involves use of mammalian cells (CHO, HEK293, Xenopus Oocytes, RBL-2H3, etc.) that are transfected to express the receptor of interest, and that are also transfected with a reporter gene construct that is coupled to activation of the receptor (for example, luciferase or beta-galactosidase behind an appropriate promoter). The cells are contacted with a test substance and the receptor agonist (ligand), such as S-1-P or di-hydro S-1-P, and the signal produced by the reporter gene is measured after a defined period of time. The signal can be measured using a luminometer, spectrophotometer, fluorimeter, or other such instrument appropriate for the specific reporter construct used. Inhibition of the signal generated by the ligand indicates that a compound is a potential antagonist for the receptor.

Another screening technique for antagonists or agonists involves introducing RNA encoding the EDG1-c polypeptide into Xenopus oocytes (or CHO, HEK 293, RBL-2H3, etc.) to transiently or stably express the receptor. The receptor oocytes are then contacted with the receptor ligand, such as S-1-P or di-hydro S-1-P, and a compound to be screened. Inhibition or activation of the receptor is then determined by detection of a signal, such as, cAMP, calcium, proton, or other ions.

Another method involves screening for EDG1-c polypeptide inhibitors by determining inhibition or stimulation of EDG1-c polypeptide-mediated cAMP and/or adenylate cyclase accumulation or dimunition. Such a method involves transiently or stably transfecting a eukaryotic cell with EDG1-c polypeptide receptor to express the receptor on the cell surface. The cell is then exposed to potential antagonists in the presence of EDG1-c polypeptide ligand, such as S-1-P or di-hydro S-1-P. The changes in levels of cAMP is then measured over a defined period of time, for example, by radio-immuno or protein binding assays (for example using Flashplates or a scintillation proximity assay). Changes in cAMP levels can also be determined by directly measuring the activity of the enzyme, adenylyl cyclase, in broken cell preparations. If the potential antagonist binds the receptor, and thus inhibits EDG1-c polypeptide-ligand binding, the levels of EDG1-c polypeptide-mediated cAMP, or adenylate cyclase activity, will be reduced or increased.

Another screening method for agonists and antagonists relies on the endogenous pheromone response pathway in the yeast, *Saccharomyces cerevisiae*. Heterothallic strains of yeast can exist in two mitotically stable haploid mating types, MATa and MATa. Each cell type secretes a small peptide hormone that binds to a G-protein coupled receptor on opposite mating-type cells which triggers a MAP kinase cascade leading to G1 arrest as a prelude to cell fusion. Genetic alteration of certain genes in the pheromone response pathway can alter the normal response to pheromone, and heterologous expression and coupling of human G-protein coupled receptors and humanized G-protein subunits in yeast cells devoid of endogenous pheromone receptors can be linked to downstream signaling pathways and reporter genes (e.g., U.S. Pat. Nos. 5,063,154; 5,482,835; 5,691,188). Such genetic alterations include, but are not limited to: (i) deletion of the STE2 or STE3 gene encoding the endogenous G-protein coupled pheromone receptors; (ii) deletion of the FAR1 gene encoding a protein that normally associates with cyclin-dependent kinases leading to cell cycle arrest; and (iii) construction of reporter genes fused to the FUS1 gene promoter (where FUS1 encodes a membrane-anchored glycoprotein required for cell fusion). Downstream reporter genes can permit either a positive growth selection (e.g., histidine prototrophy using the FUS1-HIS3 reporter), or a colorimetric, fluorimetric or spectrophotometric readout, depending on the specific reporter construct used (e.g., b-galactosidase induction using a FUS1-LacZ reporter).

The yeast cells can be further engineered to express and secrete small peptides from random peptide libraries, some of which can permit autocrine activation of heterologously expressed human (or mammalian) G-protein coupled receptors (Broach, et al, *Nature* 384: 14–16, 1996; Manfredi, et al., *Mol. Cell. Biol.* 16: 4700–4709, 1996). This provides a rapid direct growth selection (e.g., using the FUS1-HIS3 reporter) for surrogate peptide agonists that activate characterized or orphan receptors. Alternatively, yeast cells that functionally express human (or mammalian) G-protein coupled receptors linked to a reporter gene readout (e.g., FUS1-LacZ) can be used as a platform for high-throughput screening of known ligands, fractions of biological extracts and libraries of chemical compounds for either natural or surrogate ligands. Functional agonists of sufficient potency (whether natural or surrogate) can be used as screening tools in yeast cell-based assays for identifying G-protein coupled receptor antagonists. For example, agonists will promote growth of a cell with FUS-HIS3 reporter or give positive readout for a cell with FUS1-LacZ. However, a candidate compound that inhibits growth or negates the positive readout induced by an agonist is an antagonist. For this purpose, the yeast system offers advantages over mammalian expression systems due to its ease of utility and null receptor background (lack of endogenous G-protein coupled receptors), which often interferes with the ability to identify agonists or antagonists.

The present invention also provides a method for identifying new ligands not known to be capable of binding to an EDG1-c polypeptide. The screening assays described above for identifying agonists may be used to identify new ligands.

The present invention also contemplates agonists and antagonists obtained from the above described screening methods.

Examples of potential EDG1-c polypeptide receptor antagonists include peptidomimetics, synthetic organic molecules, natural products, antibodies, etc., that bind to the receptor but do not elicit a second messenger response, such that the activity of the receptor is prevented.

Potential antagonists also include proteins which are closely related to the ligand of the EDG1-c polypeptide receptor, i.e., a fragment of the ligand, which have lost biological function, and when they bind to the EDG1-c polypeptide receptor, elicit no response.

Thus in another aspect, the present invention relates to a screening kit for identifying agonists, antagonists, and ligands for EDG1-c polypeptides, comprising:
  (a) a EDG1-c polypeptide, preferably that of SEQ ID NO:2; and further preferably comprises labeled or unlabeled S-1-P or di-hydro S-1-P;
  (b) a recombinant cell expressing a EDG1-c polypeptide, preferably that of SEQ ID NO:2; and further preferably comprises labeled or unlabeled S-1-P or di-hydro S-1-P; or (c) a cell membrane expressing EDG1-c polypeptide; preferably that of SEQ ID NO:2; and further preferably comprises labeled or unlabled S-1-P or di-hydro S-1-P.

It will be appreciated that in any such kit, (a), (b), or (c) may comprise a substantial component.

As noted above, a potential antagonist is a small molecule which binds to the EDG1-c polypeptide receptor, making it inaccessible to ligands such that normal biological activity is prevented. Examples of small molecules include, but are not limited to, small peptides or peptide-like molecules.

Potential antagonists also include soluble forms of EDG1-c polypeptide receptor, e.g., fragments of the receptor, which bind to the ligand and prevent the ligand from interacting with membrane bound EDG1-c polypeptide receptors.

The screening method may simply measure the binding of a candidate compound to the polypeptide, or to cells or membranes bearing the polypeptide, or a fusion protein thereof by means of a label directly or indirectly associated with the candidate compound. Alternatively, the screening method may involve competition with a labeled competitor. Further, these screening methods may test whether the candidate compound results in a signal generated by activation or inhibition of the polypeptide, using detection systems appropriate to the cells bearing the polypeptide. Inhibitors of activation are generally assayed in the presence of a known agonist and the effect on activation by the agonist by the presence of the candidate compound is observed. Constitutively active polypeptides may be employed in screening methods for inverse agonists or inhibitors, in the absence of an agonist or inhibitor, by testing whether the candidate compound results in inhibition of activation of the polypeptide. Further, the screening methods may simply comprise the steps of mixing a candidate compound with a solution containing a polypeptide of the present invention, to form a mixture, measuring EDG-1c activity in the mixture, and comparing the EDG-1c activity of the mixture to a standard. Fusion proteins, such as those made from Fc portion and EDG-1c polypeptide, as hereinbefore described, can also be used for high-throughput screening assays to identify antagonists for the polypeptide of the present invention (see D. Bennett et al., *J. Mol. Recognition,* 8:52–58 (1995); and K. Johanson et al., *J. Biol. Chem.,* 270(16):9459–9471 (1995).

Polypeptides of the present invention may be employed in conventional low capacity screening methods and also in high-throughput screening (HTS) formats. Such HTS formats include not only the well-established use of 96- and, more recently, 384-well microtiter plates but also emerging methods such as the nanowell method described by Schullek, et al., *Anal Biochem.,* 246: 20–29 (1997).

Prophylactic and Therapeutic Methods

This invention provides methods of treating an abnormal conditions related to both an excess of and insufficient amounts of human EDG-1c receptor activity.

If the activity of human EDG-1c receptor is in excess, several approaches are available. One approach comprises administering to a subject an inhibitor compound (antagonist) as hereinabove described along with a pharmaceutically acceptable carrier in an amount effective to inhibit activation by blocking binding of ligands to the human EDG-1c receptor, or by inhibiting a second signal, and thereby alleviating the abnormal condition.

In another approach, soluble forms of human EDG-1c polypeptides still capable of binding the ligand in competition with endogenous human EDG-1c may be administered. Typical embodiments of such competitors comprise fragments of the human EDG-1c polypeptide.

In still another approach, expression of the gene encoding endogenous human EDG-1c can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression,* CRC Press, Boca Raton, Fla. (1988). Alternatively, oligonucleotides which form triple helices with the gene can be supplied. See, for example, Lee, et al., *Nucleic Acids Res* (1979) 6:3073; Cooney et al., *Science* (1988) 241:456; Dervan, et al., *Science* (1991) 251:1360. These oligomers can be administered per se or the relevant oligomers can be expressed in vivo.

For treating abnormal conditions related to an underexpression of human EDG-1c receptor and its activity, several approaches are also available. One approach comprises administering to a subject a therapeutically effective amount of a compound which activates human EDG-1c receptor, i.e., an agonist as described above, in combination with a pharmaceutically acceptable carrier, to thereby alleviate the abnormal condition. Alternatively, gene therapy may be employed to effect the endogenous production of human EDG-1c receptor by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches,* (and references cited therein) in Human Molecular Genetics, T Strachan and A P Read, BIOS Scientific Publishers Ltd. (1996).

Formulation and Administration

Peptides, such as the soluble form of human EDG-1c polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 μg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

EXAMPLES

Example 1

Yeast Cell Expression

The receptors of the present invention was constitutively expressed in *Saccharomyces cerevisiae* using the PGK1 promoter carried on a standard 2-micron-based *S. cerevisiae-E. coli* shuttle plasmid containing the gene for ampillicin resistance, the ColE1 origin of replication and the *S. cerevisiae* LEU2 gene. The human EDG-1c cDNA was modified by trimming away the 5' and 3' UTRs and subcloned into the yeast expression vector. Following introduction into yeast cells using standard yeast genetic techniques, human EDG-1c polypeptide expression was detected by western blotting using a C-terminally tagged human EDG-1c construct and antibodies to the epitope tag. Functional expression of human EDG-1c polypeptide (untagged) was determined as described in Example 9.

Example 2

Ligand Bank for Binding and Functional Assays

A bank of over 600 putative receptor ligands has been assembled for screening. The bank comprises: transmitters, hormones and chemokines known to act via a human seven transmembrane (7TM) receptor; naturally occurring compounds which may be putative agonists for a human 7TM receptor, non-mammalian, biologically active peptides for which a mammalian counterpart has not yet been identified; and compounds not found in nature, but which activate 7TM receptors with unknown natural ligands. This bank is used to initially screen the receptor for known ligands, using both functional (i.e., calcium, cAMP, microphysiometer, oocyte electrophysiology, etc., see below) as well as binding assays.

Example 3

Ligand Binding Assays

Ligand binding assays provide a direct method for ascertaining receptor pharmacology and are adaptable to a high throughput format. The purified ligand for a receptor is radiolabeled to high specific activity (50–2000 Ci/mmol) for binding studies. A determination is then made that the process of radiolabeling does not diminish the activity of the ligand towards its receptor. Assay conditions for buffers, ions, pH and other modulators such as nucleotides are optimized to establish a workable signal to noise ratio for both membrane and whole cell receptor sources. For these assays, specific receptor binding is defined as total associated radioactivity minus the radioactivity measured in the presence of an excess of unlabeled competing ligand. Where possible, more than one competing ligand is used to define residual nonspecific binding.

Example 4

Functional Assay in Xenopus Oocytes

Capped RNA transcripts from linearized plasmid templates encoding the receptor cDNAs of the invention are synthesized in vitro with RNA polymerases in accordance with standard procedures. In vitro transcripts are suspended in water at a final concentration of 0.2 mg/ml. Ovarian lobes are removed from adult female toads, Stage V defolliculated oocytes are obtained, and RNA transcripts (10 ng/oocyte) are injected in a 50 nl bolus using a microinjection apparatus. Two electrode voltage clamps are used to measure the currents from individual Xenopus oocytes in response to agonist exposure. Recordings are made in Ca2+ free Barth's medium at room temperature. The Xenopus system can be used to screen known ligands and tissue/cell extracts for activating ligands.

Example 5

Microphysiometric Assays

Activation of a wide variety of secondary messenger systems results in extrusion of small amounts of acid from a cell. The acid formed is largely as a result of the increased metabolic activity required to fuel the intracellular signaling process. The pH changes in the media surrounding the cell are very small but are detectable by the CYTOSENSOR microphysiometer (Molecular Devices Ltd., Menlo Park, Calif.). The CYTOSENSOR is thus capable of detecting the activation of a receptor which is coupled to an energy utilizing intracellular signaling pathway such as the G-protein coupled receptor of the present invention.

Example 6

Extract/Cell Supernatant Screening

A large number of mammalian receptors exist for which there remains, as yet, no cognate activating ligand (agonist). Thus, active ligands for these receptors may not be included within the ligands banks as identified to date. Accordingly, the 7TM receptor of the invention is also functionally screened (using calcium, cAMP, microphysiometer, oocyte electrophysiology, etc., functional screens) against tissue extracts to identify natural ligands. Extracts that produce positive functional responses can be sequentially subfractionated until an activating ligand is isolated identified.

Example 7

Calcium and cAMP Functional Assays

7TM receptors which are expressed in HEK 293 cells have been shown to be coupled functionally to activation of PLC and calcium mobilization and/or cAMP stimulation or inhibition. Basal calcium levels in the HEK 293 cells in receptor-transfected or vector control cells were observed to be in the normal, 100 nM to 200 nM, range. HEK 293 cells expressing recombinant receptors are loaded with fura 2 and in a single day >150 selected ligands or tissue/cell extracts are evaluated for agonist induced calcium mobilization. Similarly, HEK 293 cells expressing recombinant receptors are evaluated for the stimulation or inhibition of cAMP production using standard cAMP quantitation assays. Agonists presenting a calcium transient or cAMP fluctuation are tested in vector control cells to determine if the response is unique to the transfected cells expressing receptor.

Example 8

S-1-P-induced Ca2+ Mobilization in Untransfected HEK 293 Cells

HEK 293 cells respond to S-1-P in a concentration-dependent manner with a robust calcium mobilization response, indicating that the cells contain endogenous receptors that respond to S-1-P. FIG. 3 shows the concentration response curves for S-1-P against untransfected HEK 293 cells. The data were generated with the 96 well Fluorescent Imaging Plate Reader (FLIPR). Each point is the mean of 6–8 wells read on FLIPR.

Example 9

S-1-P-induced Reporter Gene Expression in Yeast

Figure 5:
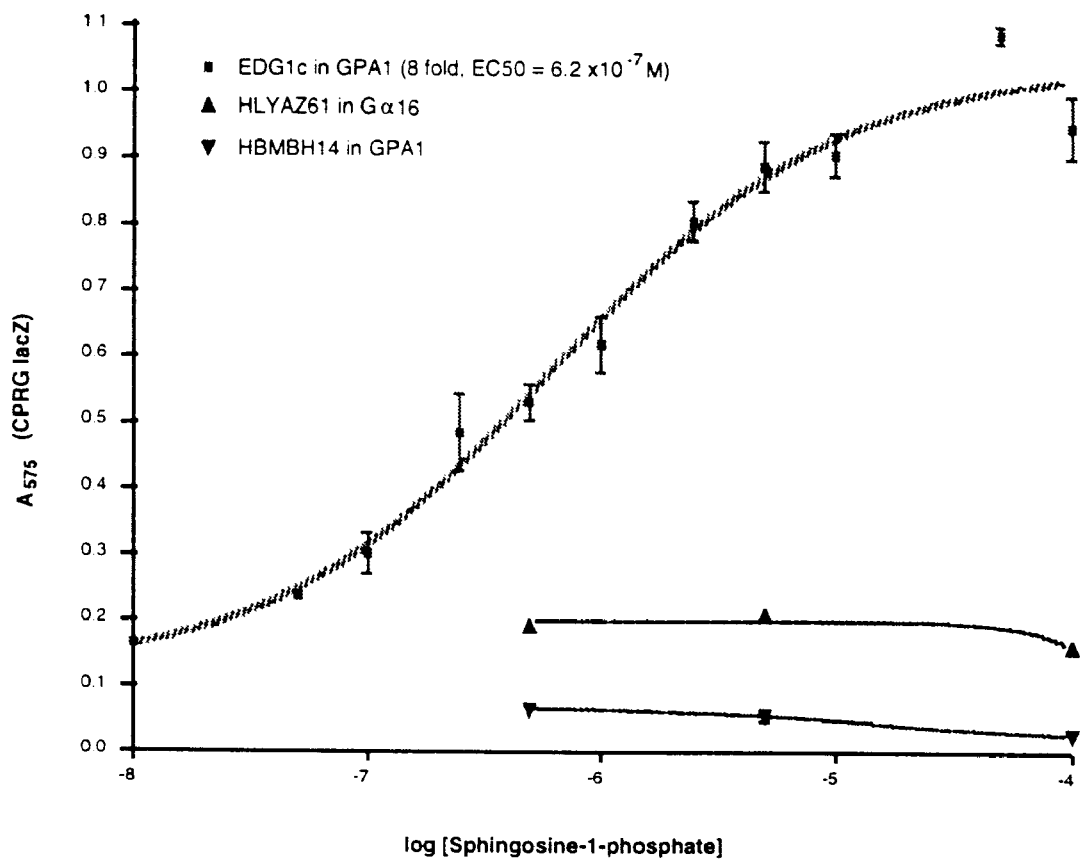
FIG. 5 shows concentration response curves for S-1-P against yeast cells containing the pathway-inducible fus1-lacZ reporter and expressing the human EDG-1c receptor in combination with GPA1 in a liquid lacZ assay format.

Human EDG-1c receptor was expressed in yeast strains containing endogenous yeast G-proteins and/or co-expressed yeast/human chimeric G proteins, and/or human G-proteins. The yeast strain(s) used contain mutations in genes in the pheromone response pathway, e.g., (i) deletion of the STE2 or STE3 gene encoding the endogenous G-protein coupled pheromone receptors; (ii) deletion of the FAR1 gene encoding a protein that normally associates with cyclin-dependent kinases leading to cell cycle arrest; and (iii) construction of reporter genes fused to the FUS1 gene promoter (where FUS1 encodes a membrane-anchored glycoprotein required for cell fusion). The downstream reporter (FUS1-LacZ) permits a colorimetric or fluorimetric readout in response to ligand. FUS1-LacZ cells expressing human EDG-1c demonstrated a receptor-dependent response to S-1-P as determined by the expression of ?-galactosidase. This response, which is shown in FIG. 5, indicates functional coupling of the human EDG-1c receptor to yeast or yeast/human chimeric G-proteins.

Example 10

Figure 6:
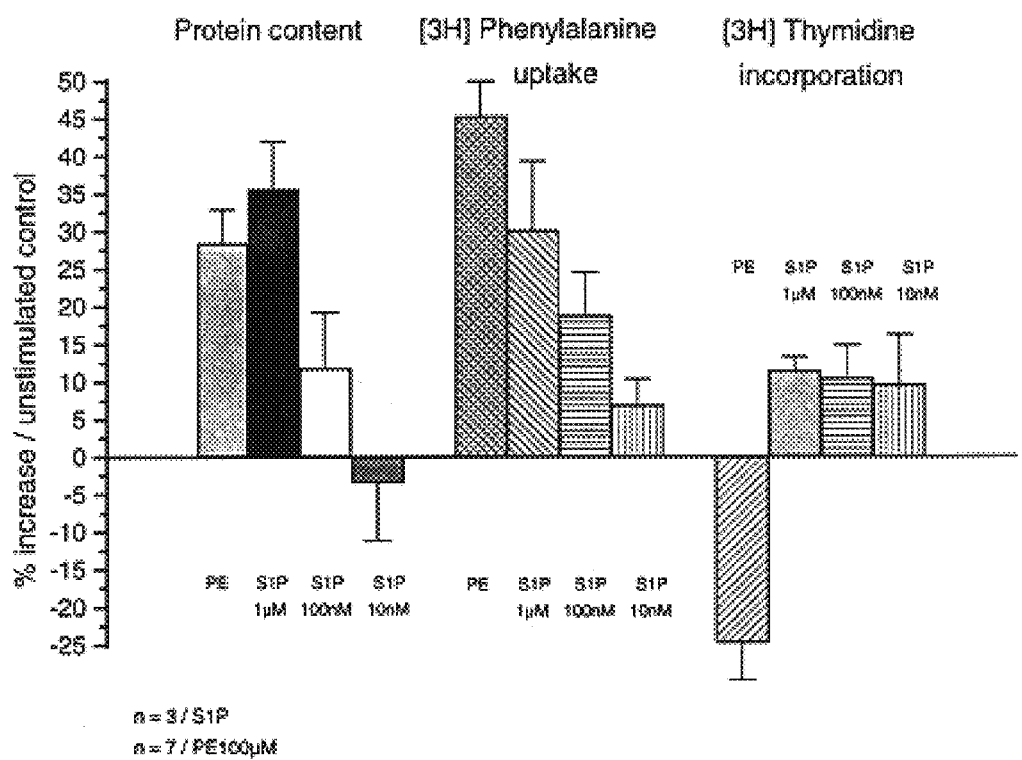
FIG. 6 shows dose dependent cellular hypertrophy in rat neonatal myocytes in culture induced by S-1-P.

S-1-P-induced a Dose Dependent Cellular Hypertrophy in Rat Neonatal Myocytes in Culture S-1-P was tested in its ability to induce hypertrophy in an in vitro neonatal cardiomyocyte model. The assessment of cardiomyocyte hypertrophy is measured using four different parameters: protein synthesis (tritiated phenylalanine incorporation and protein content increase), tritiated thymidine incorporation (evaluation of fibroblast contamination), Brain Natriuretic Peptide (BNP) release and morphological parameters. Phenylephrine (PE) at 100 $\mu$M concentration is used as internal control experiments. S-1-P was applied at 10 nM, 100 nM and 1 $\mu$M (n=3). At each concentration S-1-P induced a cellular hypertrophy with an increase of protein content, phenylalanine incorporation and BNP secretion to the control cell values. FIG. 6 shows the concentration response for S-1-P against rat neonatal cardiomyocytes. Cardiomyocytes in culture display features of myocyte hypertrophy observed in vivo, such as changes in morphology (vizualised using light microscopy after staining with crystal violet), protein content, and pattern of gene expression. For example, at 1 $\mu$M (n=3), S-1-P induced a cellular hypertrophy with an 35.6%±6.3; 30.1%±9.2 and 11.4%±1.8 increase of protein content, phenylalanine and thymidine incorporation respectively to the control cell values. BNP secretion was four fold higher in S-1-P treated cardiomyocyte vs. control.

Example 11

Human EDG1-c mRNA Expression in Human Cardiac Pathologies

Northern blot analysis was done either on 2 $\mu$g of poly A+ RNA of each sample fractionated on 1% formaldehyde-agarose gel, blotted on to a nylon membrane (Hybond N+, Amersham) and subsequently hybridized using standard methods (Sambrook, et al., 1989) with a DNA fragment containing the human EDG1-c gene. The DNA probe was labelled using (?-32P)-dCTP and the Ready-prime labeling system (Amersham). Northern blots were hybridized overnight at 65° C. and subsequently washed with 0.1× SSC, 0.1% SDS at 55° C. and exposed to X-ray film for 2–12 h. Northern blot experiments on cardiac human pathological blot membranes indicated reproducible overexpression of EDG-1 receptor mRNA in dilated cardiomyopathy and ischemic samples.

Example 12

Functional Effects of S-1-P on Isolated Perfused Heart

The functional effects of S-1-P have been examined in isolated perfused rabbit heart. S-1-P (10 nM) produced a slight negative inotropic effect as the values were at 10 min of drug administration 96.09±6 mm Hg and 84.7±6.3 mm Hg in controls versus S-1-P-treated group, respectively. An increased in AoP (aortic pressure), reflecting a vasoconstrictor effect was observed, i.e., about 30% of increase at 5 min of treatment compared to the vehicle (methanol 0.001%). A marked reduction of LVEDP (left ventricular end-diastolic pressure) was also noted.

Example 13

Figure 7:
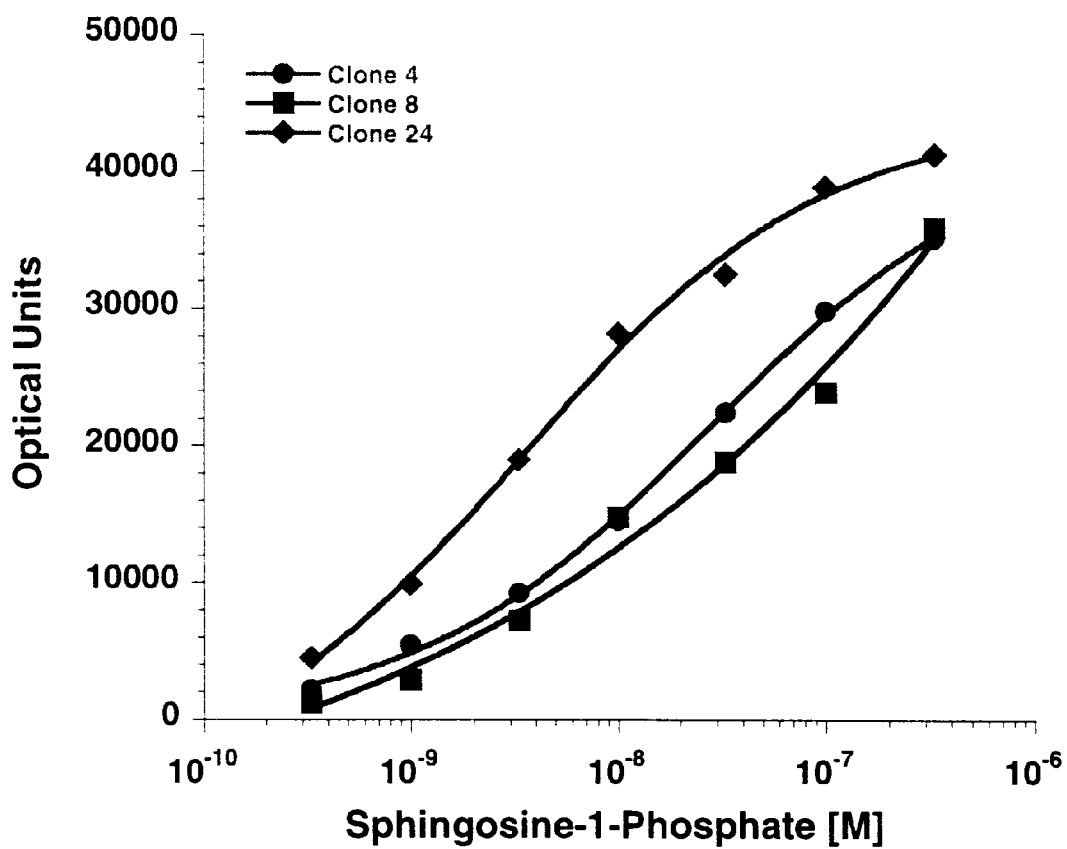
FIG. 7 shows concentration-response curves for S-1-P in RBL 2H3 cells stably transfected with the EDG-1c receptor.
Figure 8:
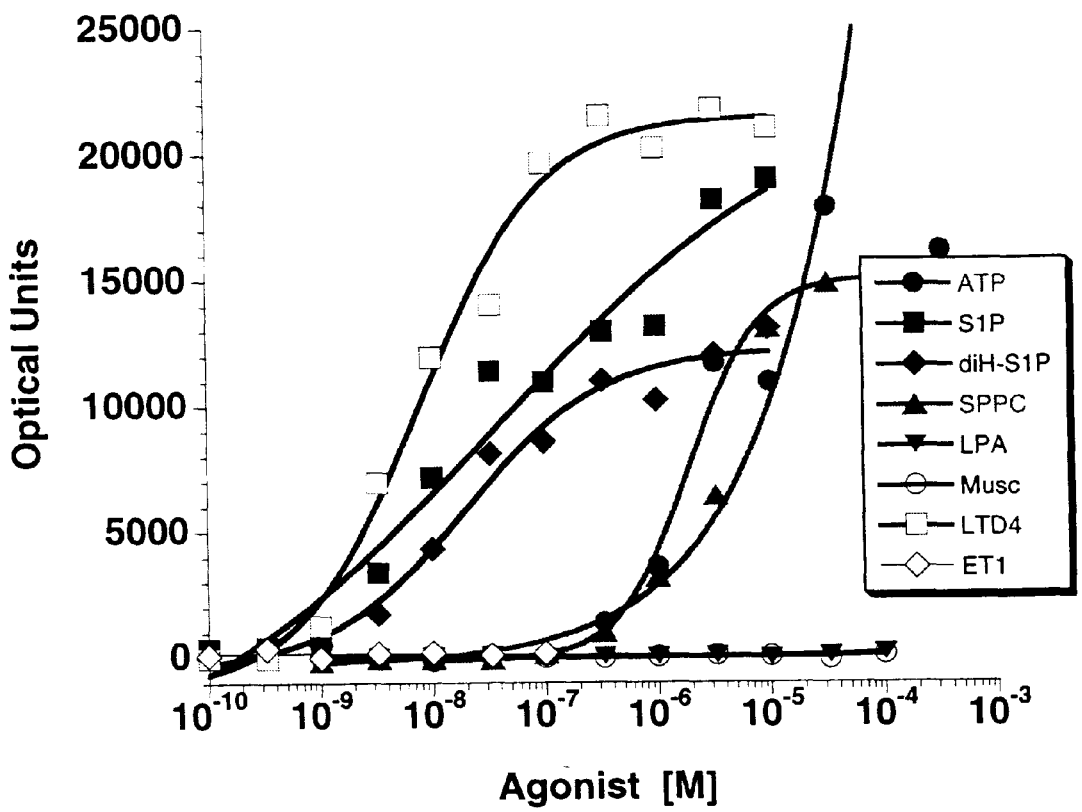
FIG. 8 shows agonist activity for a number of ligands in RBL 2H3 EDG-1c cells.

S-1-P-induced Calcium Mobilization Response in RBL 2H3 Cells Stably Transfected with Human EDG-1c Receptor Based on the results generated in FIG. 3, it was shown that an S-1-P exhibited an endogenous response in HEK 293 cells. A number of cell lines were examined to identify one that would not respond to S-1-P through an endogenous receptor. The cell line that we identified was RBL 2H3 cells. Stable cell lines of the EDG1-c receptor were prepared in RBL 2H3 cell line. The expression of functionally active clones were followed using Fluorescent imaging plate reader (FLIPR). The responses for several clones to S-1-P is presented in FIG. 7. As can be seen from this figure, the best clones respond in a concentration-dependent manner with EC$_{50}$s about 10–20 nM. The best clones were characterized further, and that is shown in FIG. 8. The cells responded with high potency through the EDG1-c receptor to S-1-P and dihydro-S-1-P with similar EC$_{50}$s in the 10–20 nM range and weakly to sphingosine phosphorylcholine (SPPC) with EC$_{50}$ in the uM range. The cells did not respond to lyso-phosphatidic acid (LPA, an EDG2 receptor ligand). Included in the figure are the responses to endogenous receptors, namely, leukotriene D$_4$ (LTD$_4$) and ATP to demonstrate that the cells were functionally in good shape. These endogenous ligands gave the expected EC$_{50}$ values for these cells. Muscarine and endogenous ligand for HEK 293, cells but not RBL 2H3 cells, did not respond.

All publications including, but not limited to, patents and patent applications, cited in this specification, are herein incorporated by reference as if each individual publication were specifically and individually indicated to be incorporated by reference herein as though fully set forth.

The above description fully discloses the invention, including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the examples provided herein are to be construed as merely illustrative and are not a limitation of the scope of the present invention in any way. The embodiments of the invention in which an exclusive property or privilege is claimed are defined as follows.

What is claimed is:

1. An isolated polynucleotide comprising a nucleotide sequence encoding the polypeptide of SEQ ID NO:2; or a nucleotide sequence complementary to said nucleotide sequence.

2. The polynucleotide as claimed in claim 1, wherein said polynucleotide is DNA or RNA.

3. The polynucleotide as claimed in claim 1, wherein said nucleotide sequence comprises SEQ ID NO:1.

4. An expression system comprising a polynucleotide capable of producing a polypeptide comprising the polypeptide sequence set forth in SEQ ID NO:2 when said expression system is in a compatible host cell.

5. A process for producing a recombinant host cell comprising the step of introducing the expression system as claimed in claim 4 into a cell, such that the host cell, under appropriate culture conditions, produces said polypeptide.

6. A recombinant host cell produced by the process as claimed in claim 5.

7. A membrane of a recombinant host cell as claimed in claim 6 comprising said polypeptide.

8. A process for producing a polypeptide comprising culturing a host cell as claimed in claim 5 under conditions sufficient for the production of said polypeptide and recovering the polypeptide from the culture.

* * * * *

SEQUENCE LISTING

<160> NUMBER OF SEQ ID NOS: 2

<210> SEQ ID NO 1
<211> LENGTH: 1149
<212> TYPE: DNA
<213> ORGANISM: Human

<400> SEQUENCE: 1

```
atggggccca ccagcgtccc gctggtcaag gcccaccgca gctcggtctc tgactacgtc      60
aactatgata tcatcgtccg gcattacaac tacacgggaa agctgaatat cagcgcggac     120
aaggagaaca gcattaaact gacctcggtg gtgttcattc tcatctgctg ctttatcatc     180
ctggagaaca tctttgtctt gctgaccatt tggaaaacca agaaattcca ccgacccatg     240
tactatttta ttggcaatct ggccctctca gacctgttgg caggagtagc ctacacagct     300
aacctgctct tgtctggggc caccacctac aagctcactc ccgcccagtg gtttctgcgg     360
gaagggagta tgtttgtggc cctgtcagcc tccgtgttca gtctcctcgc catcgccatt     420
gagcgctata tcacaatgct gaaaatgaaa ctccacaacg ggagcaataa cttccgcctc     480
ttcctgctaa tcagcgcctg ctgggtcatc tccctcatcc tgggtggcct gcctatcatg     540
ggctggaact gcatcagtgc gctgtccagc tgctccaccg tgctgccgct ctaccacaag     600
cactatatcc tcttctgcac cacggtcttc actctgcttc tgctctccat cgtcattctg     660
tactgcagaa tctactcctt ggtcaggact cggagccgcc gcctgacgtt ccgcaagaac     720
atttccaagg ccagccgcag ctctgagaag tcgctggcgc tgctcaagac cgtaattatc     780
gtcctgagcg tcttcatcgc ctgctggggca ccgctcttca tcctgctcct gctggatgtg     840
ggctgcaagg tgaagacctg tgacatcctc ttcagagcgg agtacttcct ggtgttagct     900
gtgctcaact ccggcaccaa ccccatcatt tacactctga ccaacaagga gatgcgtcgg     960
gccttcatcc ggatcatgtc ctgctgcaag tgcccgagcg gagactctgc tggcaaattc    1020
aagcgaccca tcatcgccgg catggaattc agccgcagca aatcggacaa ttcctcccac    1080
ccccagaaag acgaagggga caacccagag accattatgt cttctggaaa cgtcaactct    1140
tcttcctag                                                             1149
```

<210> SEQ ID NO 2
<211> LENGTH: 382
<212> TYPE: PRT
<213> ORGANISM: Human

-continued

<400> SEQUENCE: 2

```
Met Gly Pro Thr Ser Val Pro Leu Val Lys Ala His Arg Ser Ser Val
 1               5                  10                  15
Ser Asp Tyr Val Asn Tyr Asp Ile Ile Val Arg His Tyr Asn Tyr Thr
             20                  25                  30
Gly Lys Leu Asn Ile Ser Ala Asp Lys Glu Asn Ser Ile Lys Leu Thr
         35                  40                  45
Ser Val Val Phe Ile Leu Ile Cys Cys Phe Ile Ile Leu Glu Asn Ile
     50                  55                  60
Phe Val Leu Leu Thr Ile Trp Lys Thr Lys Lys Phe His Arg Pro Met
 65                  70                  75                  80
Tyr Tyr Phe Ile Gly Asn Leu Ala Leu Ser Asp Leu Leu Ala Gly Val
                 85                  90                  95
Ala Tyr Thr Ala Asn Leu Leu Leu Ser Gly Ala Thr Thr Tyr Lys Leu
            100                 105                 110
Thr Pro Ala Gln Trp Phe Leu Arg Glu Gly Ser Met Phe Val Ala Leu
        115                 120                 125
Ser Ala Ser Val Phe Ser Leu Leu Ala Ile Ala Ile Glu Arg Tyr Ile
    130                 135                 140
Thr Met Leu Lys Met Lys Leu His Asn Gly Ser Asn Asn Phe Arg Leu
145                 150                 155                 160
Phe Leu Leu Ile Ser Ala Cys Trp Val Ile Ser Leu Ile Leu Gly Gly
                165                 170                 175
Leu Pro Ile Met Gly Trp Asn Cys Ile Ser Ala Leu Ser Ser Cys Ser
            180                 185                 190
Thr Val Leu Pro Leu Tyr His Lys His Tyr Ile Leu Phe Cys Thr Thr
        195                 200                 205
Val Phe Thr Leu Leu Leu Leu Ser Ile Val Ile Leu Tyr Cys Arg Ile
    210                 215                 220
Tyr Ser Leu Val Arg Thr Arg Ser Arg Arg Leu Thr Phe Arg Lys Asn
225                 230                 235                 240
Ile Ser Lys Ala Ser Arg Ser Ser Glu Lys Ser Leu Ala Leu Leu Lys
                245                 250                 255
Thr Val Ile Ile Val Leu Ser Val Phe Ile Ala Cys Trp Ala Pro Leu
            260                 265                 270
Phe Ile Leu Leu Leu Leu Asp Val Gly Cys Lys Val Lys Thr Cys Asp
        275                 280                 285
Ile Leu Phe Arg Ala Glu Tyr Phe Leu Val Leu Ala Val Leu Asn Ser
    290                 295                 300
Gly Thr Asn Pro Ile Ile Tyr Thr Leu Thr Asn Lys Glu Met Arg Arg
305                 310                 315                 320
Ala Phe Ile Arg Ile Met Ser Cys Cys Lys Cys Pro Ser Gly Asp Ser
                325                 330                 335
Ala Gly Lys Phe Lys Arg Pro Ile Ile Ala Gly Met Glu Phe Ser Arg
            340                 345                 350
Ser Lys Ser Asp Asn Ser Ser His Pro Gln Lys Asp Glu Gly Asp Asn
        355                 360                 365
```

-continued

```
Pro Glu Thr Ile Met Ser Ser Gly Asn Val Asn Ser Ser Ser
    370                 375                 380
```